Figure 1:
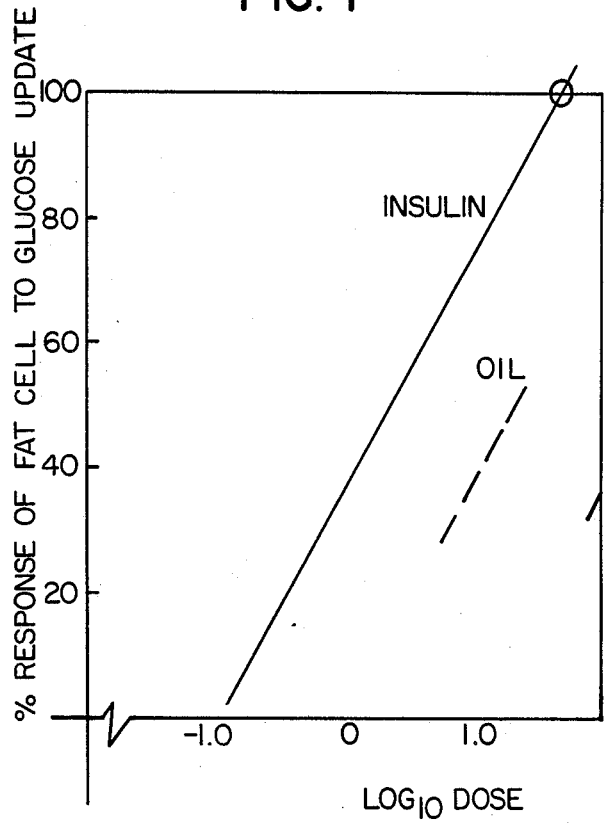

United States Patent [19]

Hakky

[11] Patent Number: 4,826,684

[45] Date of Patent: May 2, 1989

[54] COMPOSITION FOR, AND METHOD OF, TREATMENT OF DIABETES

[76] Inventor: Said I. Hakky, 8547 Merrimoor Blvd. East, Largo, Fla. 33542

[21] Appl. No.: 856,930

[22] Filed: Apr. 28, 1986

[51] Int. Cl.[4] .................... A61K 35/78; A61K 31/34; A61K 31/12; A61K 31/045

[52] U.S. Cl. ................... 424/195.1; 514/468; 514/691; 514/729; 514/866

[58] Field of Search ............ 424/195.1; 514/468, 514/729, 691, 866

[56] References Cited

U.S. PATENT DOCUMENTS 4,569,843  2/1986  Kim .......................... 424/195.1

OTHER PUBLICATIONS

Chem. Abst. 88:51025m 1978.
Chem. Abst. 93:235161n, 1980.
Chem. Abst. 88:86013h, 1978.

*Primary Examiner*—John W. Rollins

*Attorney, Agent, or Firm*—Caesar, Rivise, Bernstein, Cohen & Pokotilow, Ltd.

[57] ABSTRACT

A method of producing a composition for use in the treatment of insulin-dependent diabetes is described. The active ingredient in the composition is a mixture of terpenoids derived from an extract of the tubers of the plant *Cyperus rotundus Linn* and is administered orally to diabetic patients to provide therapeutic effects such as reducing blood sugar levels. The prepared extract can be in a powder form or in a volatile oil. A comparison of oral administration of equal volumes of the composition and insulin indicates that the composition has about 20% of the effect of insulin, which would be obviated by concentrating the composition. The composition can also be administered parenterally. In clinical trials on humans a flavor enhanced composition derived from an agneous-based paste resulted in significant therapeutic benefit with no side effects.

The production of the composition and method of treatment of a diabetic patient is also described.

3 Claims, 1 Drawing Sheet

COMPOSITION FOR, AND METHOD OF, TREATMENT OF DIABETES

This invention relates to the use of compositions found in prepared or extracted from plant sources in the fabrication of a pharmaceutically active material for the treatment particularly of insulin-dependent diabetes mellitus (IDDM).

Insulin-dependent mellitus (IDDM) is a form of diabetes in which the patient's glucose metabolism can only be controlled by injection of insulin from two to four times a day as a permanent ongoing medication. Insulin cannot of course be taken by mouth because its protein structure would be broken down by digestive mechanisms long before it arrived in the tissues for use.

Because this repeated injection requirement is so uncomfortable, some efforts have been made to find a food or medicine which can be taken orally and the active component of which survives these digestive mechanisms until it arrives in the tissues, at which location it can supplement or substitute some of the insulin requirement otherwise needed in sugar metabolism. Certain herbal remedies have been proposed, but their use is not widespread.

The present invention, however, in one aspect sets out to provide such a material of vegetable origin and based on the plant *Cyperus rotundus, Linn* which is a pantropic species grown in some oriental countries and also widely occurring as a weed, the English name of which is "Nut Grass", and the French "Souchet frond". It is a glabrous slender sedge, with an elongate underground stem, filiform with ovate-oblong tubuers. The culms are slender, triquetous, 60–150 cm-tall, and densely leafy at the base. The rays of the umbels vary from 3 to 9; they are unequal and may be simple or branching.

The plant has an elaborate underground system of stolons, tubers and roots. The tubers (with which this invention is primarily concerned, and which are also referred to herein as rhizomes) are succulent and white when young but when mature turn black.

It is well known to use the tubers for a wide range of medicinal purposes. Thus, the roots have been reported as being emmenagogue, sedative, antispasmodic, demulcent and hemostatic. Uterine disorders (amenorrhea, menorrhagia) and childbirth problems are also counteracted. It is stated moreover to be tonic, stomachic, expectorant, diuretic, antifebrile, decongestant and antirheumatic, among a long list of other qualities, and to relieve headaches or external pains, e.g. toothaches, whitlows. Hitherto, however, this well documented and ancient remedy has not been suggested as, or in, a food or medicine active against IDDM.

In one aspect the invention consists in the use of a material found in extracted or prepared from the plant *Cyperus rotundus Linn* in the preparation of a medicine or foodstuff for the treatment of insulin-dependent diabetes mellitus.

Preferably, the material is an ingestible powder, and most preferably it is prepared by drying and grinding tubers of the plant, especially the mature tubers.

The dried powder material itself has an influence on the IDDM, and in accordance with the invention it is used in the preparation of the medicine or foodstuff together with a proportion (preferably a minor proportion) of the dried and powdered gum of *Pistacia lentiscus Linn* which is used as a flavour enhancer only.

Another aspect of the invention consists in the use of the extracted volatile oil component of the tubers of *Cyperus rotundus Linn* in the preparation of a pharmaceutically active material for the treatment of IDDM.

Preferably the extraction is carried out by steam distillation of the tubers in a known procedure, yielding up to 2% of a volatile oil. Extract compositions vary with the origin and subspecies of the *Cyperus rotundus*, but the oil appears to be essentially a mixture of 10, 20 or more terpenoids, among which have been identified a sesquiterpene ketone a-cyperone (up to 50%) and significant amounts of cyperene, a tricylic sesquiterpene ($C_{15}H_{24}$) and cyperol, a tricylic alcohol, $C_{15}H_{24}O$.

The oil has been found to stimulate an increase in glucose uptake in isolated fat cells on in vitro testing, as described in more detail below.

Another aspect of the invention consists in a method of treatment of insulin-dependent diabetes consisting of orally administering a pharmaceutically effective amount of a composition having at least one terpenoid found in the plant *Cyperus rotundus Linn*.

While it is possible for the composition defined above or, where appropriate pharmaceutically acceptable salts thereof (hereinafter referred to as the "active compounds") to be administered as the raw chemical it is preferred that the active compound is presented in the form of a pharmaceutical composition.

In a further aspect of the invention there is therefore provided a pharmaceutical formulation comprising the active compound together with a pharmaceutically acceptable carrier therefor. The carrier must be "acceptable" in the sense of being compatible with the other ingredients of the formulation and not deleterious to the recipient thereof. Such carriers are solid, liquid or gaseous materials recommended for the purpose of administering the medicament.

These pharmaceutical compositions may be administered orally or parenterally (including subcutaneous, intramuscular and intravenous injection) or as a suppository or pessary. It is preferred that the compositions are administered orally. The terms formulation and composition are used synonomously.

For oral administration the pharmaceutical compositions may be presented as a draught in water or in a syrup, in capsules, cachets, boluses or tablets, as an aqueous or oleaginous solution or suspension or in suspension in a syrup, such suspension optionally including suspending agents or as an oil-in-water or water-in-oil emulsion. Where desirable or necessary flavouring, sweetening, preserving, thickening or emulsifying agents may be included in the formulation.

Tablets may contain the active compound as a powder or granules optionally mixed with binders, lubricants, inert diluents or surface-active or dispersing which are useful in such formulations.

All the above formulations are produced by processes which comprise bringing into association the active compound and one or more carriers.

The invention will be further described with reference to the following examples of preparation, in vitro testing and clinical test.

EXAMPLE I

Tubers of *Cyperus rotundus Linn* were dried to constant weight in a vacuum oven at room temperature and powdered for extraction.

EXTRACTIONS

A. Aqueous Extract. 50 gms of powder was boiled with water for four hours. The mixture was filtered and the aqueous extract was evaporated to dryness on a rotary evaporator below 45° C. The extract yielded 3.9 grams of solid - 7.6% w/w of original plant material.

B. Ethanolic Extract. 20 gms of powder was extracted by maceration at room temperature for one week with redistilled alcohol. The mixture was filtered and evaporated as before. The extract yeilded 0.33 gms of solid - 6.5% w/w of original plant material.

C. Preparation of volatile oil. 50 gms of powder was steam distilled in the B.P. "determination of volatile oil" apparatus. The pure oil separated from the condensed steam in the side arm. The water was run off and rejected and the oil collected in a glass vial. The yield was 1 ml per 50 grams of powder - 2% v/w.

Thin-Layer-Chromatographic (TLC) Analysis of Oil

The oil was subject to micro-analysis on silica gel precoated/aluminium plates using a toluene/ethyl acetate as solvent and visulised with 5% vanillin in concentrated $H_2SO_4$. It was a complex mixture of terpenoids, containing at least 15 separate compounds. These substances gave a colour spectrum containing blue, purple, red, orange and yellow colours when reacted with the spray reagent to indicate the composition and type of oils.

Stimulation of Lipogenesis: (A measure of Insulin-like action)

Mature male rats were killed and the distal fronds of the epidydimal fat pad were dissected, minced and digested in collagenase. The cells per ml of the filtrate were determined and the cell suspension was used to determine the conversion of $C^{14}$-glucose to lipids by incubation and scintillation counting. Insulin was used as a standard drug for comparison with the plant extracts. Both the standard drug and the volatile oil demonstrated activity.

It was seen that the plant material contains a volatile oil producing effects upon the biochemistry of sugar conversion to fat. The oil formed 2% by volume of the plant material. Analysis of the oil demonstrated that it was a complex mixture of terpenoids. Reference is now made to the drawing FIG. 1 which depicts a graph showing percentage response of fat cells to glucose uptake versus the logarithim of the dose of active ingredient per ml of solution. It can be seen from the graph that the response for the oil and insulin are substantially linear. However, in absolute terms the oil stimulated a 50% increase in glucose uptake by isolated fat cells in a dose of 7.9 g/ml media whilst insulin provided a similar response at a dose of 1.6 g/ml. Therefore with the ingredients shown the insulin is 5 times as effective as the oil and consequently oil concentrated by a factor of five will provide a similar response as insulin.

EXAMPLE 2

Clinical Test

A powder comprising *Cyperus rotundus Linn* tubers dried and powdered (42 g) *Pistacia lentiscus Linn*, gum dried and powdered with sufficient water to form a paste. 5 ml of the paste was administered four times daily, after meals, to a 7 year old boy weighing about 25 kg suffering from IDDM and treated with two injections daily of 8 units of insulin, resulting in a dosage of about 1-2 grams Cyperus powder/kg body weight/day. After six weeks of such treatment a flattening of the blood glucose curve was observed and the rate of injection of insulin was halved without adverse effect. It was observed that the insulin requirement varied according to the level of physical exercise of the patient. When no physical exercise was undertaken the reduction was 70% whereas with 1 to 2 active exercises per day, such as swimming, running or football the reduction reached 100%. After 1 year of clinical trials excluding Pistacia and Iris no ill effects or change was observed. It was concluded that *Cyperus rotundus Linn* was the active ingredient. Further clinical trials were carried out with Cyperus only and the results were consistent with laboratory testing.

Further extensions of the trial to 18 m. produced no harmful side effects.

The method of manufacture of the product, method of treatment using the product and the actual product for use is original, novel, inventive and useful. Although the exact mechanism of behaviour of the active ingredient is not fully understood it is believed that the sensitivity of glucose receptors to insulin are enhanced, or glucose receptor production is increased or glucose is metabolised in cells where insulin is not needed, for example, in some muscle cells.

It will be understood that various modifications may be made to the examples and compositions hereinbefore described without departing from the scope of the invention. For example, the active ingredient may be terpenoids derived from any suitable parent source other than the tubers of the plant *Cyperus rotundus Linn*. Also, such an active ingredient may be derived synthetically and used to treat diabetes in the same way as with the plant derived active ingredient. Accordingly, such alternative compositions are believed to be within the scope of the invention.

I claim:

1. A method of treatment of persons afflicted with insulin-dependent diabetes comprising the steps of administering to said persons a therapeutic amount of a composition having at least one terpenoid found in the plant *Cyperus rotundus Linn* in a pharmaceutically effective amount in a pharmaceutically acceptable carrier to a diabetic.

2. A method of treatment as claimed in claim 1, including the step of administering said composition orally.

3. A method of treatment as claimed in claim 1, including the step of monitoring the glucose levels of the diabetic and correlating the glucose levels with the dosage of the composition administered.

* * * * *